United States Patent [19]
Monticello

[11] Patent Number: 5,496,729
[45] Date of Patent: * Mar. 5, 1996

[54] PROCESS FOR THE DESULFURIZATION AND THE DESALTING OF A FOSSIL FUEL

[75] Inventor: Daniel J. Monticello, The Woodlands, Tex.

[73] Assignee: Energy BioSystems Corporation, The Woodlands, Tex.

[*] Notice: The portion of the term of this patent subsequent to Oct. 18, 2011, has been disclaimed.

[21] Appl. No.: 298,921

[22] Filed: Aug. 31, 1994

Related U.S. Application Data

[63] Continuation of Ser. No. 876,187, Apr. 30, 1992, Pat. No. 5,356,813.

[51] Int. Cl.$^6$ .......................... C10G 32/00; C10G 29/20; C02F 3/00; C02F 3/02
[52] U.S. Cl. ...................... 435/282; 435/281; 435/252.1; 210/601; 210/620; 208/237; 208/47; 44/624
[58] Field of Search ................................... 435/282, 281, 435/252.1; 210/601, 620; 208/237, 47; 44/624

[56] References Cited

U.S. PATENT DOCUMENTS

| | | |
|---|---|---|
| 2,975,103 | 3/1961 | Kirshenbaum . |
| 4,206,288 | 6/1980 | Detz et al. . |
| 4,283,270 | 8/1981 | McHale . |
| 4,562,156 | 12/1985 | Isbister et al. . |

(List continued on next page.)

FOREIGN PATENT DOCUMENTS

| | | |
|---|---|---|
| 396832A1 | 10/1989 | European Pat. Off. . |
| 401922A1 | 5/1990 | European Pat. Off. . |
| 0441462 | 8/1990 | European Pat. Off. . |
| 409314A1 | 10/1990 | European Pat. Off. . |
| 0396832 | 11/1990 | European Pat. Off. . |
| 445896A2 | 5/1991 | European Pat. Off. . |
| 441462A2 | 5/1991 | European Pat. Off. . |
| 0436508 | 7/1991 | European Pat. Off. . |
| 0445896 | 9/1991 | European Pat. Off. . |
| 70020176 | 1/1976 | Japan . |
| WO92/11343 | 7/1992 | WIPO . |
| WO92/16602 | 10/1992 | WIPO . |
| WO92/19700 | 11/1992 | WIPO . |

OTHER PUBLICATIONS

Omori et al., "Desulfuization of Dibenzothiophene by Corynebacterium sp. Strain SY1," *Applied and Environmental Microbiology*, 58:911–915, (1992).

Khalid et al., "Bioprocessing of Coal and Oil–Water Emulsions and Microbial Metabolism of Dibenzothiophene (DBT)," *Resources, Conservation and Recycling*, 5:167–181, (1991).

(List continued on next page.)

*Primary Examiner*—William H. Beisner
*Assistant Examiner*—T. J. Reardon
*Attorney, Agent, or Firm*—Hamilton, Brook, Smith & Reynolds

[57] ABSTRACT

This invention relates to an integrated method for the desulfurization and desalting of a fossil fuel, comprising the steps of: (a) contacting a fossil fuel with; (i) a sufficient amount of an aqueous solution capable of depleting the fossil fuel of forms of water soluble salt contaminants; and (ii) an effective amount of a biocatalyst capable of depleting the fossil fuel of forms of sulfur-bearing organic molecules; (b) incubating the above mixture whereby; (i) the fossil fuel is significantly depleted of forms of water soluble salt contaminants; and (ii) the biocatalytic agent selectively catalyzes carbon-sulfur bonds in sulfur-bearing organic molecules generating a significant amount of water-soluble inorganic sulfur molecules; both reactions occurring without depleting the fossil fuel of combustible organic molecules; and (c) separating the aqueous component from the fossil fuel component, the fossil fuel now being significantly reduced in sulfur and salt contamination and the aqueous component now being significantly enriched with inorganic salts and inorganic sulfur molecules.

9 Claims, 3 Drawing Sheets

U.S. PATENT DOCUMENTS

| | | |
|---|---|---|
| 4,618,348 | 11/1986 | Hayes et al. . |
| 4,632,906 | 12/1986 | Kopacz . |
| 4,659,670 | 4/1987 | Stevens et al. . |
| 4,808,535 | 2/1989 | Isbister . |
| 4,851,350 | 7/1989 | Stevens et al. . |
| 4,861,723 | 8/1989 | Madqavkar . |
| 4,954,229 | 9/1990 | Kim et al. . |
| 5,002,888 | 3/1991 | Kilbane . |
| 5,232,854 | 8/1993 | Monticello .............................. 435/282 |
| 5,297,625 | 3/1994 | Premuzic et al. . |
| 5,356,813 | 10/1994 | Monticello .............................. 435/282 |
| 5,358,869 | 10/1994 | Kilbane ................................... 435/282 |
| 5,358,870 | 10/1994 | Monticello et al. ..................... 435/282 |

OTHER PUBLICATIONS

Dordick et al., "Enzymatic Catalysis on Coal–Related Compounds in Organic Media: Kinetics and Potential Commerical Applications," *Resources, Conservation and Recycling,* 5:195–209, (1991).

Kilbane, J. J., "Desulfurization of Coal: the Microbial Solution," *Trends in Biotechnology,* 7(4):97–101, (1989).

Kitchell, et al., "Microbial Oxidation of Sulfur in Dibenzothiophene," Proc. Bioprocess Fossil Fuels Workshop, Bayer Ed., (1989).

Pifferi, et al., "Biodesolforazione Degli Oli Combustibili: un Contributo Innovativo per la tutela dell'ambiente," La Rivista dei Combustibili, XLIII:177–184, (1989).

Beck, et al., "Mikrobiologische Kohleentschwefelung," *Acta Biotechnol.,* 8(1):87–92, (1988).

Bhdra, et al., "Microbial Desulphurization of Heavy Oils and Bitumen," *Biotech. Adv.,* 5:1–27, (1987).

Monticello, et al., "Plasmid–Mediated Degradation of Dibenzothiophene by Pseudomonas Species," *Applied and Environmental Microbiology,* 49:756–760, (1985).

Ibister and Kobylinski, "Microbial Desulfurization of Coal.," *Coal Sci. Technol.,* 9:627–641, (1985).

Monticello and Finnerty, "Microbial Desulfurization of Fossil Fuels," *Ann. Rev. Microbiol.,* 39:371–389, (1985).

Hartdegen et al., "Micobial Desulfurization of Petroleum," *Chem. Eng. Pro.,* 80(5):63–67, (1984).

Kargi and Robinson, "Microbial Oxidation of Dibenzothiophene by the Theromophilic Organism Sulfolobus Acidocaldarius," *Biotechnology and Bioengineering,* 26:687–690, (1984).

Bertrand et al., "Microbial Degradation of Crude Oil in Sea Water in Continuous Culture," *Biotechnology Letters,* 5(8):567–572, (1983).

Eckart et al., "Mikrobielle Entschwefelung von Erdöl und schweren Erdölfraktionen," *ZBl, Mikrobiol.,* 137:270–279, (1982).

Sagardia et al., "Degradation of Benzothiophene and Related Compounds by a Soil Pseudomonas in an Oil–Aqueous Environment," *Applied Microbiology,* 29(6):722–725, (1975).

Waterman, L. C., "Crude Desalting: Why and How," *Hydrogen Processing,* 44(2):133–138, (1965).

Speight, J. G., Fuel Science and Technology Handbook, Marcel Dekker, Inc., Chapter 5, 1981.

Kim et al., "Degradation of Organic Sulfur Compounds and the Reduction of Dibenzothiophene to Biphenyl and Hydrogen Sulfide," *Biotechnology Letters,* 12(10):761–764, (1990).

Kilbane, J. J., "Sulfur–Specific Microbial Metabolism of Organic Compounds," *Resources, Conservation and Recycling,* 3:69–79, (1990).

Monticello and Kilbane, "Practical Considerations in Biodesulfurization of Petroleum," IGT's Third International Symposium on Gas, Oil, Coal and Environmental Biotechnology, (1990).

Lee and Yen, "Sulfur Removal from Coal Through Multiphase Media Containing Biocatalysts," *J. Chem. Techn. Biotechnol.,* 48:71–79, (1990).

Ochman, et al., "Mineralization of S from Dibenzothiophene, Dibenzothiophene Sulphone and Benzene Sulphonic Acid by Soil Isolates," Microbios., 63:79–91, (1990).

Stoner, et al., "Modification of Water–Soluble Coal–Derived Products by Dibenzothiophene–Degrading Microorganisms," Applied and Environmental Microbiology, 56:2667–2676, (1990).

PROCESS FOR THE DESULFURIZATION AND THE DESALTING OF A FOSSIL FUEL

This application is a continuation of application Ser. No. 07/876,187, filed Apr. 30, 1992, which is now patented as U.S. Pat. No. 5,356,813.

BACKGROUND OF THE INVENTION

Salt contaminants in fossil fuels can create problems in refinery processes which can be costly to rectify. For example, these contaminants can plug downstream equipment, can form products that are corrosive to refinery equipment, and can interfere with chemical processing.

Various inorganic salts suspended in fossil fuels, such as petroleum, are usually removed by vigorous washing with water at the production site and prior to refining. There presently are three general approaches for the desalting of fossil fuels. All three require the contact of the fossil fuel with water. The selection of a particular process depends on the type of salt dispersion and the properties of the particular fossil fuel. For example, simple brine suspensions can be removed from fossil fuel by heating under pressure sufficient to prevent vapor loss [90°–150° C. (200°–300° F.)/50–250 psi], then allowing the material to settle and separate in a large vessel.

Alternatively, fresh water can be combined with the fossil fuel to form emulsions which solubilize the salts from the oil into the water. The aqueous fossil fuel emulsion can separate aided by its passage through a tower packed with sand, gravel or similar material. Emulsions can also be broken by addition of treating agents such as soaps, fatty acids, sulfonates, and long-chain alcohols. Electrostatic precipitators can employ a high potential electric field across a settling vessel to coalescence and break emulsions, in which case dissolved salts and impurities are removed with the water. As a result of the physical washing of crude oil, the salt concentration in the wash water can become quite high and unamendable to biological activity.

Sulfur contaminants of oil, as well, can be problematic. The presence of sulfur has been correlated with corrosion of pipeline, pumping, and refining equipment, and with premature breakdown of combustion engines. Sulfur also poisons many catalysts which are used in the refining and combustion of fossil fuels. Moreover, the atmospheric emission of sulfur combustion products such as sulfur dioxide leads to the form of acid deposition known as acid rain. Acid rain has lasting deleterious effects on aquatic and forest ecosystems, as well as on agricultural areas located downwind of combustion facilities. Monticello, D. J. and W. R. Finnerty, (1985) *Ann. Rev. Microbiol.* 39:371–389. Regulations such as the Clean Air Act of 1964 require the removal of sulfur, either pre- or post-combustion, from virtually all petroleum-based fuels. Conformity with such legislation has become increasingly problematic due to both the rising need to utilize lower grade, higher-sulfur fossil fuels as clean-burning, low-sulfur petroleum reserves become depleted, and the progressive reductions in sulfur emissions required by regulatory authorities. Monticello, D. J. and J. J. Kilbane, "Practical Considerations in Biodesulfurization of Petroleum", *IGT's 3d Intl. Symp. on Gas, Oil, Coal, and Env. Biotech.*, (Dec. 3–5, 1990) New Orleans, La.

There are no available physicochemical procedures to desulfurize crude oil, although there are several methods for reducing sulfur in refinery intermediates. One widely-used technique is hydro-desulfurization, or HDS. In HDS, the fossil fuel is contacted with hydrogen gas at elevated temperature and pressure, in the presence of a catalyst. The removal of organic sulfur is accomplished by reductive conversion of sulfur compounds to $H_2S$, a corrosive gaseous product which is removed by stripping. This technique cannot be applied to crude oil because of the fragile and volatile nature of some components of this material. As with other desulfurization techniques, HDS is done as a separate procedure from desalinization, requiring additional equipment.

Pretreatment desulfurization and desalting of fossil fuel prior to later refinery processing currently requires separate and distinct procedures and equipment. Various authors and inventors have proposed biological processes for the desulfurization of coal and crude oil, as a separate unit process in refineries. A need exists to develop a more efficient method for desulfurization and desalinization. This need grows progressively more urgent as petroleum companies look to cut costs in light of increased processing costs, as well as increased federal and state restrictions. Any elimination of the need for some of the equipment presently used for desulfurization and desalinization, or consolidation of the equipment used, would increase efficiency and lower costs.

SUMMARY OF THE INVENTION

This invention relates to an integrated method for the desulfurization and desalting of a fossil fuel, comprising the steps of: (a) contacting a fossil fuel with; (i) a sufficient amount of an aqueous solution capable of depleting the fossil fuel of forms of water soluble salt contaminants; and (ii) an effective amount of a biocatalyst capable of depleting the fossil fuel of forms of sulfur-bearing organic molecules; (b) incubating the above mixture whereby; (i) the fossil fuel is significantly depleted of forms of water soluble salt contaminants; and (ii) the biocatalytic agent selectively catalyzes carbon-sulfur bonds in sulfur-bearing organic molecules generating a significant amount of water-soluble inorganic sulfur molecules; both reactions occurring without depleting the fossil fuel of combustible organic molecules; and (c) separating the aqueous component from the fossil fuel component, the fossil fuel now being significantly reduced in sulfur and salt contamination and the aqueous component now being significantly enriched with inorganic salts and inorganic sulfur molecules.

The invention described herein directly addresses the problems posed by the limitations of current techniques for desulfurizing and desalting fossil fuels. The instant invention provides for the removal of a significant amount of sulfur while simultaneously eliminating salt contaminants. The new integrated process eliminates the need for some subsequent desulfurization procedures and apparati.

In the present invention, the biocatalytic agent used comprises a biocatalyst which, while in a solution with a salt concentration equal to that encountered in aqueous oil washing procedures, is capable of liberating sulfur in the form of inorganic sulfur from sulfur-bearing organic molecules dissolved in hydrocarbons by sulfur-specific oxidative cleavage. Any biocatalyst with said properties would be useful in the process of the present invention. A preferred biocatalyst comprises a culture of Rhodococcus bacteria, ATCC No. 53968. This biocatalyst provides for the removal of a significant proportion of the total sulfur from a fossil fuel and is compatible with aqueous desalting procedures.

A further advantage to the instant invention is its efficacy. Present methods require that desulfurization and desalting processes be distinct and separate, often times having the processing facilities in different locations, requiring transportation of the partially processed fossil fuel for further processing. The present method is an integrated process, requiring the integration of a biocatalytic desulfurization step with known aqueous desalting technologies. By integrating these processes, desulfurization and desalting can be accomplished in the field, at collection points or at the refinery in one processing system.

DESCRIPTION OF THE INVENTION

This invention is based on the integration and use of a biocatalytic agent which is capable of selectively liberating sulfur from organic sulfur molecules, in conjunction with an aqueous desalting technique and the unexpected experimental finding that biocatalytic desulfurization could proceed in the high-salt solutions associated with crude desalting. Both of these processes require water to remove the undesirable components. This integration provides for the synergistic desulfurization and desalting of the fossil fuel.

The preferred physicochemical desalting method for use in the instant integrated method is aqueous desalting. Aqueous desalting involves water washing of crude oil by first heating the salt-containing fossil fuel to reduce its viscosity and surface tension and for easier mixing which facilitates later separation of the aqueous component. See Waterman, L., *Hydrocarbon Processing*, 44(2):133–138 (1965). The upper temperature limit depends on the type of fossil fuel. An aqueous solution is added and the mixture passes through a mixing valve or, in a preferred embodiment, a continuous stirred tank reactor (CSTR), to achieve intimate contact of the water with the fossil fuel. In addition, chemicals additives can be used to adjust the pH of the wash water.

Figure 1:
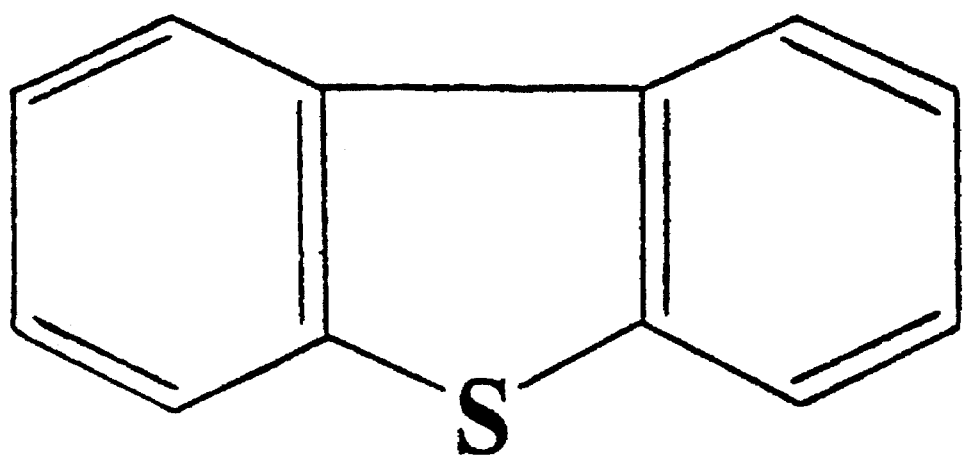
FIG. 1 is a schematic illustration of the structural formula of dibenzothiophene.

The condensed-ring sulfur-bearing heterocycle dibenzothiophene (DBT), shown in FIG. 1, is representative of a variety of sulfur-bearing compounds which can account for a significant percentage of the total organic sulfur in certain fossil fuels. This class of molecules is the most difficult for most technology to remove. See Shih et al, AICHE Abstract No. 264B, (1990), (complete text available upon request from the American Institute of Chemical Engineers). This molecule is commonly used in desulfurization studies and can account for as much as 70% of the total sulfur content of West Texas crude oil, and up to 40% of the total sulfur content of some Middle East crude oils. Monticello, D. J. and W. R. Finnerty, (1985) *Ann. Rev. Microbiol.* 39:371–389. Biocatalysts have been shown to desulfurize DBT as well as simpler molecules (e.g. mercaptans and thiophenes) and other more complex structures.

No naturally occurring bacteria or other microbial organisms have been identified which are capable of totally degrading or desulfurizing DBT. Thus, when released into the environment, DBT and related complex heterocycles tend to persist for long periods of time and are not significantly biodegraded. Gundlach, E. R. et al., (1983) Science 221:122–129.

Figure 2:
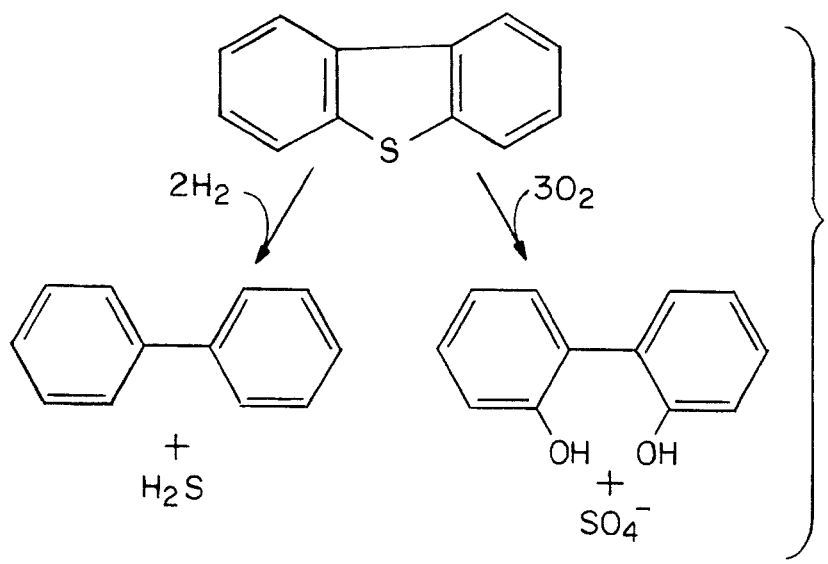
FIG. 2 is a schematic illustration of the cleavage of dibenzothiophene by oxidative and reductive pathways, and the end products thereof.

However, several investigators have reported the genetic modification of naturally-occurring bacteria into mutant strains capable of catabolizing DBT. Kilbane, J. J., (1990) *Resour. Cons. Recycl.* 3:69–79, Isbister, J. D., and R. C. Doyle, (1985) U.S. Pat. No. 4,562,156, and Hartdegan, F. J. et al., (May 1984) *Chem. Eng. Progress* 63–67. For the most part, these mutants desulfurize DBT nonspecifically, and release sulfur in the form of small organic sulfur breakdown products. Thus, a portion of the fuel value of the oil is lost through this microbial action. Isbister and Doyle reported the derivation of a mutant strain of Pseudomonas which appeared to be capable of selectively liberating sulfur from DBT, but did not elucidate the mechanism responsible for this reactivity. Kim et al, (Kim et al., *Biotechnology Letters,* 12(10):761–764 1990), have demonstrated the feasibility of using bacteria for reductive conversion of sulfur to hydrogen sulfide. As shown in FIG. 2, there are at least two possible pathways which result in the specific release of sulfur from DBT, oxidative and reductive pathways.

Figure 3:
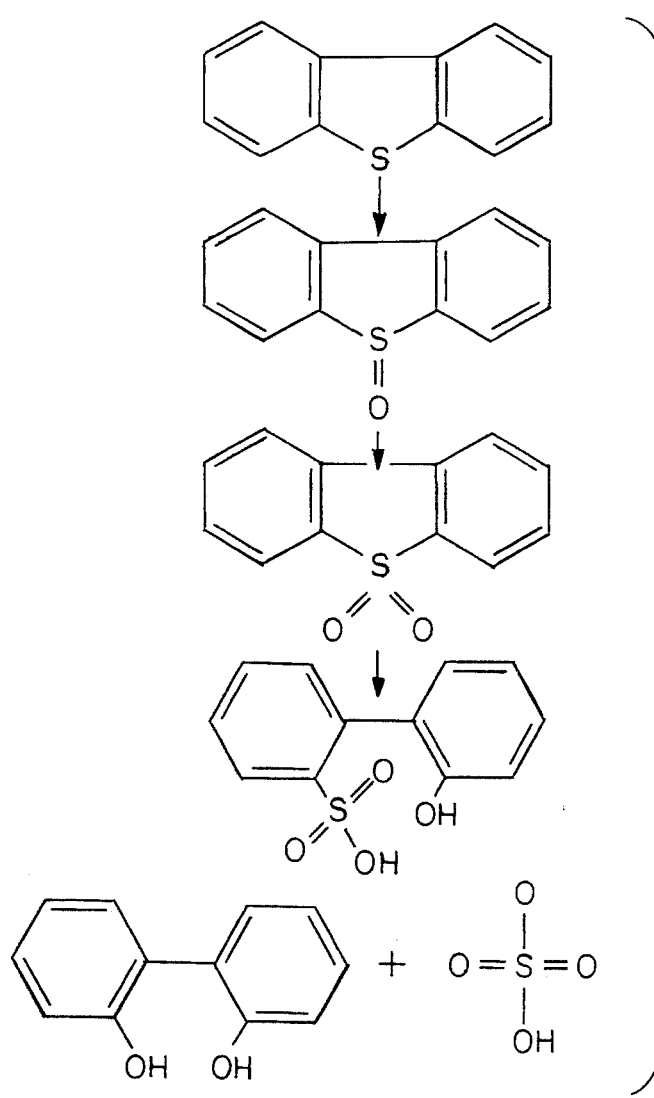
FIG. 3 is a schematic illustration of the stepwise oxidation of dibenzothiophene along the proposed "4S" pathway of microbial catabolism.

Kilbane recently reported the mutagenesis of a mixed bacterial culture, producing one which appeared capable of selectively liberating sulfur from DBT by the oxidative pathway. This culture was composed of bacteria obtained from natural sources such as sewage sludge, petroleum refinery waste water, garden soil, coal tar-contaminated soil, etc., and maintained in culture under conditions of continuous sulfur deprivation in the presence of DBT. The culture was then exposed to the chemical mutagen 1-methyl-3-nitro-1-nitrosoguanidine. The major catabolic product of DBT metabolism by this mutant culture was hydroxybiphenyl; sulfur was released in an inorganic water-soluble form, presumably sulfate, and the hydrocarbon portion of the molecule remained essentially intact. Based upon these results, Kilbane proposed that the "4S" catabolic pathway summarized in FIG. 3 was the mechanism by which these products were generated. The designation "4S" refers to the reactive intermediates of the proposed pathway: sulfoxide, sulfone, sulfonate, and the liberated product sulfate. Kilbane, J. J., (1990) *Resour. Cons. Recycl.* 3:69–79, the teachings of which are incorporated herein by reference.

Subsequently, Kilbane has isolated a mutant strain of Rhodococcus from this mixed bacterial culture. This mutant, ATCC No. 53968, which is also known as IGTS8, is a preferred biocatalytic agent for use with the instant method of desulfurization and desalting, as it has been determined to be capable of divesting complex, condensed-ring heterocycles, such as DBT, of sulfur while in medium that is essentially fossil fuel or brine in content. Its use is therefore synergistic with aqueous desalting. The isolation of this mutant is described in detail in U.S. Pat. No. 5,104,801, issued to Kilbane (Apr. 14, 1992), the teachings of which are incorporated herein by reference. Rhodococcus sp. ATCC 53968 was deposited with the American Type Culture Collection, 12301 Parklawn Drive, Rockville, Md. 20852, USA on Nov. 28, 1989. The pathway, mechanism and enzymology for microbial desulfurization has not been characterized. The 4S pathway proposed by Kilbane (1990) and others is speculative in nature and the attributes of the biocatalyst is unknown. It is well established, however, that many enzymes are sensitive to high salt concentrations, and many are inactivated at salt concentrations well below those encountered in desalting operations. Consequently, it was believed that the desalting/desulfurization process described here would not work prior to the carrying out the experiments described herein. Therfore, the results obtained were unexpected.

Any biocatalyst which provides for the removal of a significant proportion of the total sulfur from a fossil fuel while in the high salt enviroment of the aqueous desalting procedures is useful in the method of the present invention. Biocatalytic agents include enzymes or enzyme complexes and bacteria. In a preferred embodiment of the present invention, *Rhodococcus rhodochrous* bacteria is used.

In another embodiment of the present invention, Rhodococcus bacteria ATCC No. 53968 is prepared by conventional fermentation under aerobic conditions, such as may be accomplished using a bioreactor and a suitable nutrient medium, comprising a conventional carbon source such as dextrose or glycerol. In order to generate maximal biocatalytic activity, it is important that the bacteria be maintained in a state of sulfur deprivation. Optionally, this may be accomplished using a medium lacking a source of inorganic sulfate, but supplemented with DBT or a liquid petroleum sample with a high relative abundance of sulfur heterocycles. A finely divided slurry of coal particles can be used similarly.

When the culture has attained a sufficient volume and/or density, the fossil fuel to be desulfurized is contacted with it. Alternatively, the bacteria or the associated enzymes can be concentrated and preserved for later use. The ratio of biocatalyst to the substrate fossil fuel in need of desulfurization can be varied widely, depending on the desired rate of reaction, and the levels and types of sulfur-bearing organic molecules present. Suitable ratios of biocatalyst to substrate can be ascertained by those skilled in the art through no more than routine experimentation. Preferably, the volume of biocatalyst will not exceed one half the total incubation volume.

The combined biocatalyst and fossil fuel mixture or aqueous fossil fuel emulsion and biocatalyst mixture are allowed to incubate under conditions suitable for biocatalytic action, for a sufficient period of time for the desired degree of desulfurization to occur. It will be noted that the proposed "4S" pathway requires that oxygen be supplied to the biocatalyst during the desulfurization incubation. The oxygen required can be supplied prior to or during the incubation, using conventional bubbling or sparging techniques. It is preferable to capitalize on the greater capacity of liquid fossil fuel (compared to aqueous liquids) to carry dissolved oxygen by supplying the oxygen directly to the liquid fossil fuel prior to contact with the biocatalyst. This can be accomplished by contacting the liquid fossil fuel with a source of air, oxygen-enriched air, pure oxygen, or by supplementing the liquid fossil fuel with an oxygen-saturated perfluorocarbon liquid.

The rate of desulfurization can optionally be enhanced by agitating or stirring the mixture of biocatalyst and substrate during the desulfurization incubation. The desulfurization rate can be further accelerated by conducting the incubation at a suitable temperature. Temperatures between about 10° C. and about 60° C. are suitable; ambient temperature is preferred. However, any temperature between the pour point of the fossil fuel and the temperature at which the biocatalyst is inactivated can be used.

Several suitable techniques for monitoring the rate and extent of desulfurization are well-known and readily available to those skilled in the art. Baseline and timecourse samples can be collected from the incubation mixture, and prepared for a determination of the residual organic sulfur in the substrate fossil fuel, normally by allowing the fuel to separate from the aqueous biocatalyst phase. The disappearance of sulfur from substrate hydrocarbons such as DBT can be monitored using X-ray fluorescence (XRF) or a gas chromatograph coupled or atomic emission spectrometric (GC/AES, or flame spectrometry) detection system. Flame spectrometry is the preferred analytical detection system, as it allows the operator to directly visualize the disappearance of sulfur atoms from combustible hydrocarbons by monitoring quantitative or relative decreases in flame spectral emissions at 392 nm, the wavelength characteristic of atomic sulfur. It is also possible to measure the decrease in total organic sulfur in the substrate fossil fuel, by subjecting the unchromatographed samples to flame spectrometry or by XRF.

After the desalting and desulfurizing reactions the processed fossil fuel is transferred to a decanter or settler which provides for a quieting zone to allow time for the wash water to settle. In electrostatic desalting, the decanter or settler is equipped with electrodes to provide a high voltage electrostatic field. The electrostatic field aids water droplet agglomeration and settling. The desalted/desulfurized fossil fuel leaves the top of the settler. Wash water along with contaminants are withdrawn from the bottom. Additional stages are used to get the desired reduction of solids and other contaminants.

Figure 4:
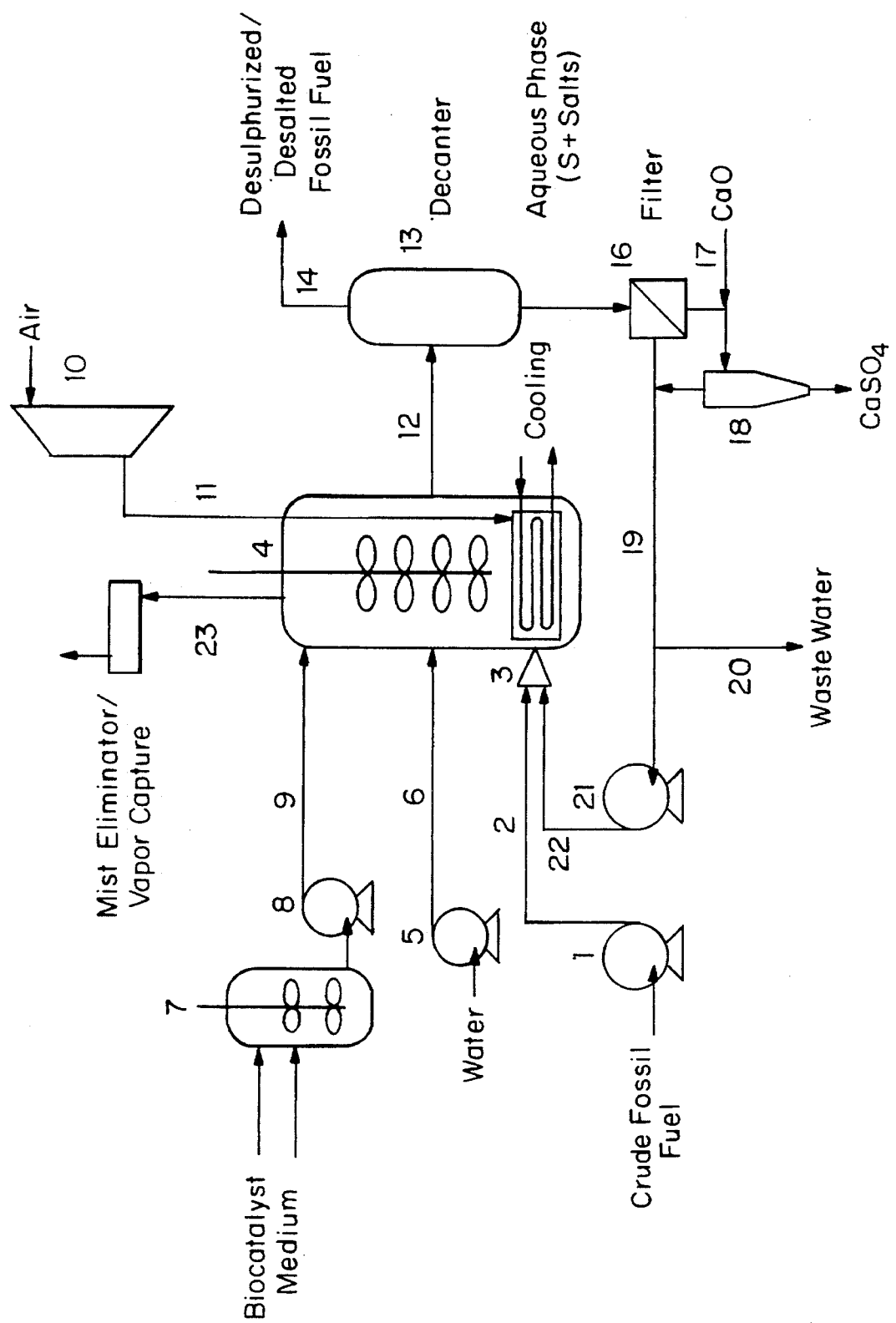
FIG. 4 is an overview of the processing of a typical fossil fuel oil sample, in the form of a flow chart diagram, through an integrated aqueous desalting/biocatalytic desulfurization process.

FIG. 4 is a schematic flow diagram of the integrated process of the present invention for biocatalytic desulfurization and desalting of fossil fuel. Fossil fuel in need of desulfurization and desalting is fed from feed 1 through line 2 to injection port 3 and into reaction vessel 4 for processing. The reaction vessel used is preferably the CSTR type reaction vessel mentioned previously.

Aqueous solution 5 is introduced through line 6, and is contacted with the fossil fuel in reaction vessel 4 whereby an aqueous fossil fuel emulsion is formed. A sufficient amount of aqueous solution is introduced to allow for the water-induced solubilization of salts. Simultaneous with the addition of the aqueous solution, the fossil fuel is contacted with a biocatalyst which is fed from bioreactor 7.

An aqueous culture of the microbial biocatalytic agent can be prepared by fermentation in bioreactor 7, using culture conditions sufficient for the growth and biocatalytic activity of the particular micro-organism used. As stated previously, in order to generate maximal biocatalytic activity, it is important that the biocatalyst culture be maintained in a state of sulfur deprivation. This can be effectively accomplished by using a nutrient medium which lacks a source of inorganic sulfate, but is supplemented with DBT or a fossil fuel sample with a high relative abundance of sulfur heterocycles. A particularly preferred microbial biocatalyst comprises a culture of mutant *Rhodococcus rodocrous* bacteria, ATCC No. 53968. This biocatalytic agent can advantageously be prepared by conventional fermentation techniques comprising aerobic conditions and a suitable nutrient medium which contains a carbon source, such as glycerol or glucose. Alternatively, the biocatalyst can be prepared elsewhere and delivered to the desulfurization/desalting reaction vessel, in which case 7 represents a biocatalyst storage or holding tank. The ratio of biocatalyst to aqueous emulsion (substrate) can be varied widely, depending on the desired rate of reaction, and the levels and types of sulfur-bearing organic molecules present. Suitable ratios of biocatalyst to substrate can be ascertained by those skilled in the art through no more than routine experimentation. Preferably, the volume of biocatalyst will not exceed about one-half the total volume in the reaction vessel (i.e., the substrate accounts for at least about 50% of the combined volume).

In addition, it is important that the reaction vessel be maintained at temperatures and pressures which are sufficient to maintain a reasonable rate of biocatalytic desulfurization and desalting. For example, the temperature of the vessel should be between about 10° C. and about 60° C., preferably between 20° C. and about 30° C. The pressure within the vessel should be at least sufficient to maintain an appropriate level of dissolved oxygen in the substrate petroleum liquid. However, the pressure and turbulence within the vessel should not be so high as to cause shearing damage to the biocatalyst.

As discussed above and shown in FIG. 3, oxygen is consumed during biocatalytic desulfurization; accordingly, oxygen 10 may be introduced through line 11, and contacted with the fossil fuel in reaction vessel 4, whereby oxygen tension in the fossil fuel is sufficiently increased to permit biocatalytic desulfurization to proceed. In this manner, the instant process allows the practitioner to capitalize on the greater capacity of fossil fuel (over aqueous liquids) to carry dissolved oxygen. For example, oxygen is ten times more soluble in octane than in water. Pollack, G. L., (1991) *Science* 251:1323–1330. Thus, oxygen can be effectively delivered to the biocatalyst than it would be by, for example, sparging air into the reaction mixture during biocatalysis. The source of oxygen (10) can be air, oxygen-enriched air, pure oxygen, an oxygen-saturated perfluorocarbon liquid, etc. Additional oxygen can be delivered to the reaction by incorporating a side stream recycle loop or other system to add additional gas.

Optionally, any volatile exhaust gasses which form in the headspace of the reaction vessel can be recovered through line 23.

As a result of catalysis taking place in reaction vessel 4, the organic sulfur content of the petroleum liquid is reduced and the inorganic sulfur content of the aqueous phase is correspondingly increased. After processing has reached an appropriate level, the reaction mixture is fed through line 12 to decanter 13 where the mixture is allowed to settle. The desulfurized/desalted fossil fuel will collect in the upper zone of decanter 13 where it is drawn off through line 14. This processed fossil fuel is then subjected to any additional steps which may be required to produce the desired fuel product (i.e., subsequent refining).

It may be desirable to recycle the biocatalyst and as much of the water as possible. Retrieval of the biocatalyst can be accomplished by using biocatalyst immobilized within the reactor vessel, which obviates the need to add or separate the biocatalyst. The immobilized biocatalyst can be immobilized on any inert particle by methods known in the art. See Albertsson, P. A., *Partition of Cell Particles and Macromolecules*, Wiley-Interscience (1971).

Recovery of the biocatalyst can be accomplished by retrieving the immobilized biocatalyst which has settled in decanter 13 through line 15, and retaining it on filter 16 allowing waste water to pass through line 17. The retained biocatalyst is then fed through line 19 to feed 21, where it is mixed with any fresh, sulfur-free nutrient medium and/or any fresh ATCC No. 53968 culture, which may be required to reconstitute or replenish to the desired level of biocatalytic activity.

The recovered biocatalytic agent is delivered through line 22 to injection ports 3, where it reenters the reaction vessel 4 and is contacted with additional fossil fuel liquid in need of desalting and biocatalytic treatment, entering the reaction vessel through injection ports 3 in the manner described previously. It is desirable to monitor and control the rates of reactants entering and products being removed from the reaction vessel, as maintaining substantially equivalent rates of entry and removal will maintain conditions (e.g., of pressure) sufficient for biocatalysis within the vessel. In this manner, a continuous stream of desulfurized and desalted fossil fuel liquid is generated, without the need to periodically pump the contents of the reaction vessel into a settling chamber where phase separation takes place, as described in Madkavkar, A. M. (1989) U.S. Pat. No. 4,861,723, and Kirshenbaum, I. (1961) U.S. Pat. No. 2,975,103.

Alternative means to remove aqueous inorganic salts and thereby regenerate the aqueous solution can also be employed. Suitable alternatives include treatment with an ion exchange resin or treatment with an agent capable of removing salts by precipitation. Suitable agents include calcium oxide to form insoluble gypsum as shown in FIG. 4. High sulfur water is treated with calcium hydroxide in line 17. The gypsum which is formed is removed by centrifuge 18 and the water is recycled. Other examples of suitable regeneration means include treatment with semipermeable ion exchange membranes and electrodialysis.

The progress of biocatalytic desulfurization of the fossil fuel liquid within the vessel can be monitored using conventional techniques, which are readily available to those skilled in the art. Baseline samples can be collected from the substrate before it is exposed to the biocatalyst, for example from sampling ports located on the reaction vessel 4. Post-catalytic samples can be collected from the product petroleum liquid which collects within the reaction vessel through sampling ports located in the vessel wall, or a sampling valve located at a decanting port located on the decanter. The disappearance of sulfur from substrate hydrocarbons such as DBT can be monitored using a XRF or gas chromatograph coupled with atomic emission spectrometric (GC/AES, or flame spectrometry) detection systems. Flame spectrometry is the preferred detection system, as it allows the operator to directly visualize the disappearance of sulfur atoms from combustible hydrocarbons by monitoring quantitative or relative decreases in flame spectral emissions at 392 nm, the wavelength characteristic of atomic sulfur. It is also possible to measure the decrease in total organic sulfur in the substrate fossil fuel, by subjecting the unchromatographed samples to flame spectrometry. If the extent of desulfurization is insufficient, the desulfurized petroleum liquid collected from line 45 can optionally be reintroduced through line 3 and subjected to an additional cycle of biocatalytic treatment. Alternatively, it can be subjected to an alternative desulfurization process, such as hydro-desulfurization (HDS), a treatment using hydrogen gas.

In other preferred embodiments of the present method, an enzyme or array of enzymes sufficient to direct the selective cleavage of carbon-sulfur bonds can be employed as the biocatalyst. Preferably, the enzyme(s) can be obtained from ATCC No. 53968 or a derivative thereof. This enzyme biocatalyst can optionally be used in carrier-bound form. Suitable carriers include killed "4S" bacteria, active fractions of "4S" bacteria (e.g., membranes), insoluble resins, or ceramic, glass, or latex particles.

EXEMPLIFICATION

Desulfurization of Sulfur-Bearing Hydrocarbons at High Salt Concentrations

Rhodococcus IGTS8 cells were grown in a minimal medium consisting of basal salts (2.44 g/l $KH_2$, $PO_4$, 5.57 g/l $Na_2PO_4$, 2 g/l $MgCl_2$-$H_2O$, 0.001 g/l $CaCl_2$-$2H_2O$, 0.001 g/l $FeCl_3$-$6H_2O$) and glycerol (20 mm), pH 7.0 with 20 mm dimethyl sulfoxide (DMSO). The cells were washed with basal salts solution and assayed for the ability to desulfurize dibenzothiophene (DBT) in the presence of increasing concentrations of salt. Desulfurization activity was determined by monitoring the accumulation of 2-hydroxy biphenyl (2-HBP), the product of DBT desulfurization.

Gibb's assay was used to determine the quantity of 2-HBP produced. Two 5 ml aliquots of culture were placed in two test tubes to measure absorbance. The absorbance was read at 600 nm and cell density was adjusted to obtain 1.00 absorbance. 50 ml of a saturated solution of DBT sulfone, in ethanol, was added to one of the tubes, 50 ml of ethanol to the control tube and both tubes were vortexed. The two tubes were then incubated, with occasional shaking, for 60 minutes at 30° C. The pH was adjusted to 8.0 in both tubes using 10% solution of $Na_2CO_3$ in distilled water.

Gibbs reagent (2,6-dichloro-quinone-4-chloroimide; obtained from Sigma Chemical Co.) was dissolved in 10 ml absolute ethanol in a test tube, and promptly protected from light by wrapping the tube in foil. After the incubation step, 50 μm of the above described reagent was added to both tubes. After a 30 minute incubation at room temperature the tube was centrifuged to pellet cells and debris. The appearance of the blue product indicating a reaction between Gibb's reagent and 2-HBP was monitored by measuring the increase in optical absorbance of the assay mixture at 610 nm, relative to the $A_{610}$ of a sample containing phosphate buffer rather than supernatant. Results were expressed as units of absorbance per hour, per unit of cell material (one unit of cell material is defined as the amount of cell/cell envelope suspension which, when suspended in water, yields an $A_{600}$ of 1.0).

Results of this study are summarized in Table 1.

TABLE 1

| % NaCl | Enzyme Activity* |
|---|---|
| 0 | 1.65 |
| 0.5 | 1.5 |
| 1 | 1.95 |
| 2 | 1.93 |
| 4 | 1.04 |
| 5 | 1.14 |
| 6 | .99 |

*ppm 2-HBP product produced/$10^8$ cells/hour

These results show that the biocatalyst can desulfurize hydrocarbons in solutions with salt concentrations of at least 6%, which is well above the salt concentrations encountered in oil washing (desalting) solutions. Prior to these experiments, microbial desulfurization of coal, petroleum or model compounds had only been attempted with growing cells or cells suspended in the low salt (basal salts) medium. Since enzyme activity is often severely inhibited by high salts concentration and no information was available on the pathway mechanism or enzymology of microbial desulfurization, the fact that the system was active in salt concentrations of up to 6% was unexpected and unpredictable.

Equivalents

Those skilled in the art will recognize, or be able to ascertain using no more than routine experimentation, many equivalents to the specific embodiments of the invention described herein. These and all other such equivalents are intended to be encompassed by the following claims.

I claim:

1. A process for reducing the amount of organic sulfur and inorganic salts from a fossil fuel containing organic sulfur compounds and inorganic salts, comprising the steps of:

(a) contacting the fossil fuel with an aqueous phase containing a biocatalyst having sulfur-specific carbon-sulfur bond cleavage ability, thereby forming a fossil fuel and aqueous phase mixture said biocatalyst comprising a bacterial organism or bacterial cell-free fractions;

(b) maintaining the mixture under conditions sufficient for cleavage of the carbon-sulfur bonds of the organic sulfur compounds, by said biocatalysts to form inorganic sulfur compounds, and for water-induced solubilization of said inorganic salts and said inorganic sulfur compounds to occur; and (c) separating the fossil fuel having a reduced organic sulfur and inorganic salt content from the resulting aqueous phase, whereby the resulting aqueous phase has a concentration greater than about 0.5 percent by weight of said inorganic salts.

2. The process of claim 1 wherein the fossil fuel is contacted with oxygen prior to step (a) to establish conditions sufficient for cleavage of carbon-sulfur bonds.

3. The process of claim 1 wherein the resulting aqueous phase is a brine.

4. The process of claim 1 wherein the fossil fuel is a liquid hydrocarbon.

5. The process of claim 4 wherein the fossil fuel is a liquified hydrocarbon.

6. The process of claim 1 wherein the biocatalyst is an immobilized biocatalyst.

7. The process of claim 1 wherein the biocatalyst cleaves the carbon-sulfur bond by an oxidative pathway.

8. The process of claim 7 wherein the biocatalyst is a bacterial microorganism.

9. The process of claim 7 wherein the biocatalyst is a cell-free fraction of a bacterial microorganism.

\* \* \* \* \*